(12) United States Patent
Appelt et al.

(10) Patent No.: US 6,589,793 B1
(45) Date of Patent: Jul. 8, 2003

(54) MEASUREMENT DEVICE FOR THE MEASUREMENT OF THE ABSOLUTE POLARISATION OF ALKALI METAL ATOMS

(75) Inventors: Stephan Appelt, Jülich (DE); Timur Unlu, Haan (DE); Nadim Jone Shah, Linnich-Boslar (DE)

(73) Assignee: Forschungszentrum Julich GmbH, Julich (DE)

( * ) Notice: Subject to any disclaimer, the term of this patent is extended or adjusted under 35 U.S.C. 154(b) by 55 days.

(21) Appl. No.: 09/590,533

(22) Filed: Jun. 8, 2000

(30) Foreign Application Priority Data

Jun. 18, 1919 (DE) .......................................... 199 28 032

(51) Int. Cl.[7] .......................... G01N 33/20; G01N 21/17
(52) U.S. Cl. ........................... 436/73; 422/83; 436/173; 436/183; 436/79
(58) Field of Search .......................... 436/73, 173, 183, 436/79; 422/82.09, 83, 91

(56) References Cited

U.S. PATENT DOCUMENTS

| 5,227,722 A | 7/1993 | Kostyk et al. ............... 324/304 |
| 5,617,860 A | 4/1997 | Chupp et al. ............. 128/653.4 |

FOREIGN PATENT DOCUMENTS

| GB | 2 078 972 | 1/1982 | .......... G01N/24/08 |

OTHER PUBLICATIONS

C. Martin et al, Nucl. Instrum. Methods Phys. Res. A 1993, 335, 233–238.*
B. Jaduszliwer et al, Phys. Rev. A 1993, 48, 2102–2107.*
C. Martin et al, AIP Conf. Proc. 1994, 293, 146–150.*
Z. Wu et al, Acta Optica Sinica 1995, 15, 683–688.*
M. P. Augustine et al, Mol. Phys. 1996, 89, 737–752.*
D. V. Kuoriyanov et al, SPIE 1996, 2802, 47–53.*
M. A. Bouchiat et al, J. Phys., Lett. 1984, 45, 523–532.*
C. C. Bradley et al, Rev. Sci. Instrum. 1990, 61, 2097–2101.*
W. J. Cummings et al, Phys. Rev. A: At. Mol., Opt. Phys. 1995, 51, 4842–4851.*
W. F. Buell et al, Appl. Phys. B: Lasers Opt. 1995, 60, S227–S231.*
P. Minguzzi et al, Nuovo Cimento B 1966, 46, 145–162.*

(List continued on next page.)

*Primary Examiner*—Arlen Soderquist
(74) *Attorney, Agent, or Firm*—Pearne & Gordon LLP

(57) ABSTRACT

The invention concerns a device for the determination of the absolute polarisation of alkali metal atoms. The device can inter alia be used for the diagnosis of alkali metal polarisation in a polariser for inert gases. The device includes a detection laser, which together with a $\lambda/4$ plate creates circularly polarised light. A sensor for the measurement of the light absorbed by the sample of the polariser is provided. A Helmholtz coil pair serves for the creation of a static magnetic field $B_0$. An oscillating magnetic field is created with an RF coil. A gradient coil serves for the creation of a linear magnetic field gradient. Various optical components are present. An electronic processor effects the determination of the absolute polarisation of the alkali metal atoms. All the said components with the exception of the Helmholtz coils are firmly mounted onto a platform which can be moved parallel to the direction of the $B_0$ field. Means for controlling the temperature of the laser for the detection of the polarisation of the alkali metal atoms are provided. The means for controlling the temperature of the laser for the detection of the polarisation of the alkali metal atoms include a temperature sensor, with which the temperature of the laser is measured, a heating/cooling device, with which the laser is heated or cooled, and also a control device, which controls the heating/cooling device depending on the measured temperature of the laser, so that the temperature of the laser is held constant. Compared to the state of the art, faster and better measurement results can thus be achieved.

16 Claims, 2 Drawing Sheets

OTHER PUBLICATIONS

Figure 1:
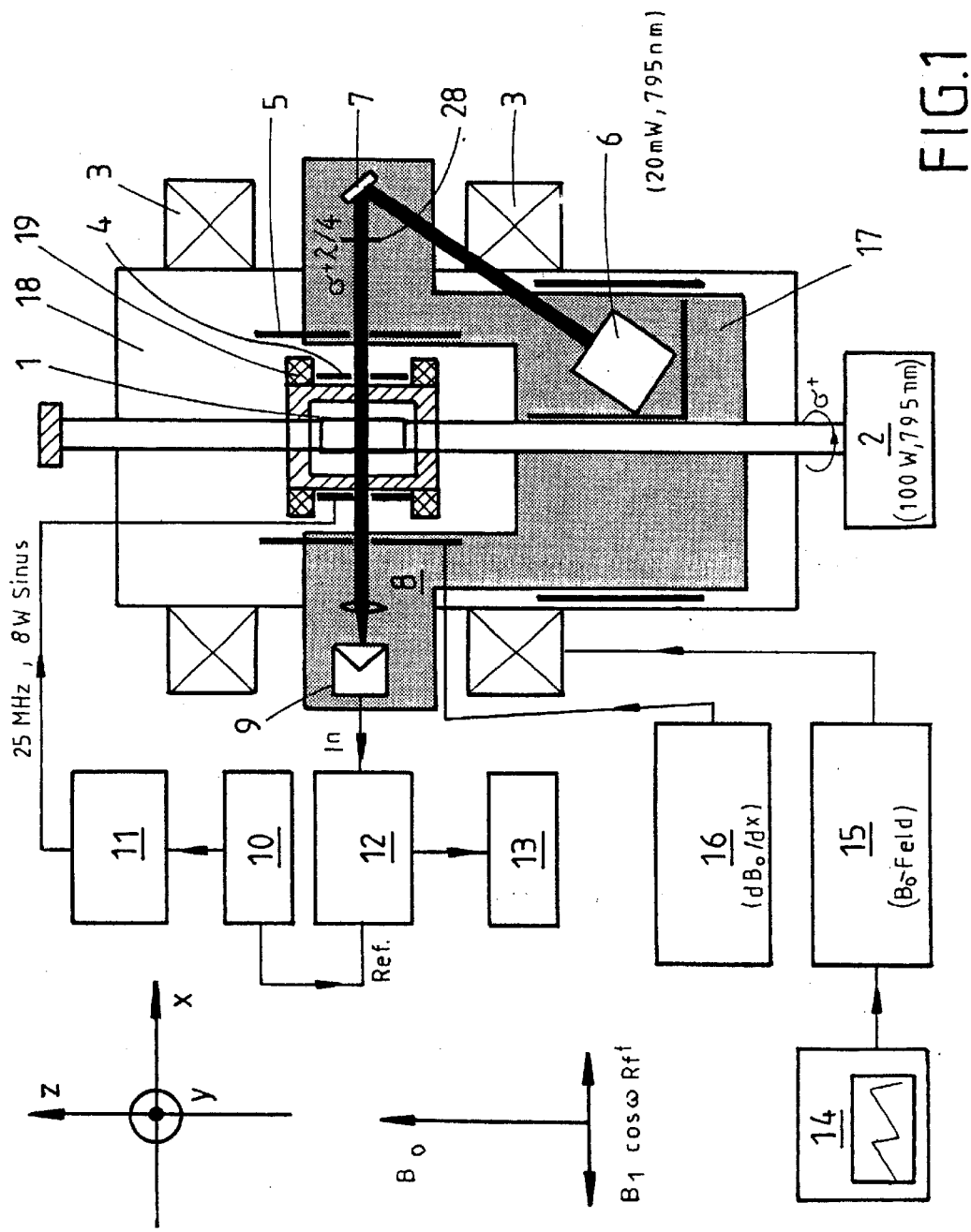

J. Haas et al, Z. Phys. 1967, 206, 1–17.*
A. Gozzini et al, Nuovo Cimento B 1967, 49, 185–193.*
J. Liran et al, Opt. Commun. 1979, 31, 169–173.*
S. Appelt et al, Phys. Rev. A: At. Mol., Opt. Phys. 1998, 58, 1412–1439.*
A. B.–A. Baranga et al, Phys. Rev. A: At. Mol., Opt. Phys. 1998, 58, 2282–2294.*
A. B.–A. Baranga et al, Phys. Rev. Lett. 1998, 80, 2801–2804.*
S. Appelt et al, Appl. Phys. Lett. 1999, 75, 427–429.*

* cited by examiner

MEASUREMENT DEVICE FOR THE MEASUREMENT OF THE ABSOLUTE POLARISATION OF ALKALI METAL ATOMS

FIELD OF THE INVENTION

The invention relates to devices and methods for measuring the absolute polarization of alkali metal atoms wherein the operation of a detection laser is improved by controlling the laser operating temperature and/or current. The polarized alkali metal atoms are contained within a sample cell disposed within magnetic fields, and the intensity of the detection laser light after passage through the sample cell is measured to determine the polarization.

BACKGROUND TO THE INVENTION

Recent developments in magnetic resonance tomography (MRT) and in magnetic resonance spectroscopy (NMR) with polarised inert gases can be expected to yield applications in medicine, in physics and in materials sciences. High nuclear spin polarisation levels in inert gases can be achieved by optical pumping using alkali metal atoms, as can be seen from the paper by Happer et al., Phys. Rev. A, 29, 3092 (1984). Typically at present, the alkali metal atom rubidium is used in the presence of an inert gas and nitrogen. In this way, it is possible to achieve a nuclear spin polarisation of ca. 20 percent in the inert gas xenon ($^{129}$Xe). Such a nuclear spin polarisation is ca. 100,000 times greater than the equilibrium polarisation in clinical magnetic resonance tomographs. The consequent drastic increase in the signal-to-noise ratio explains why in the future new possible applications are expected in medicine, science and technology.

Polarisation is understood to mean the degree of alignment (ordering) of the spin of atomic nuclei or electrons. For example, 100 percent polarisation means that all nuclei or electrons are oriented in the same way. A magnetic moment is associated with the polarisation of nuclei or electrons.

Polarised xenon is for example inhaled by a person or injected into him. 10 to 15 seconds later, the polarised xenon collects in the brain. Using magnetic resonance tomography, the distribution of the inert gas in the brain is established. The result is used for further analyses.

The choice of the inert gas depends on the particular application. $^{129}$Xenon displays a large chemical shift if xenon is for example adsorbed on a surface, then its resonance frequency changes significantly. Furthermore, xenon dissolves in fat-loving (i.e. lipophilic) liquids. When such properties are desired, xenon is used.

The inert gas helium is almost insoluble in liquids. The isotope $^3$He is therefore regularly used when cavities are concerned. The lungs of a person are an example of such a cavity.

Some inert gases have valuable properties other than the aforesaid. Thus for example the isotopes $^{83}$Krypton, $^{21}$Neon and $^{131}$Xenon have a quadrupole moment, which is for example of interest for experiments in fundamental research, namely in surface physics. However, these inert gases are very expensive, so that these are unsuitable for applications in which larger amounts are used.

From the paper "B. Driehuys et al., Appl. Phys. Lett., 69, 1668 (1996), the polarisation of inert gases in the following way is known.

Using a laser and, a λ/4 plate positioned in the light beam from the laser, circularly polarised light is produced, that is to say light in which the angular momentum i.e. spin of the photons all point in the same direction. The angular momentum of the photons is transferred to the electrons of alkali metal atoms. Hence the spins of the electrons of the alkali metal atoms display a large deviation from the thermal equilibrium. Consequently, the alkali metal atoms are polarised. As a result of a collision of an alkali metal atom with an atom of an inert gas, the polarisation of the electron spin of the alkali metal atom is transferred to the nuclear spin of the inert gas. Polarised inert gas is thus produced.

Alkali metal atoms are used as these have a large optical dipole moment, which interacts with the light. Further, alkali metal atoms each have one free electron, so that no disadvantageous interactions between two and more electrons per atom or molecule can arise.

Caesium would be a particularly suitable alkali metal atom, which Is superior to rubidium for the production of polarised xenon. However, at present there are no lasers available with sufficiently high power, such as would be needed for the polarization of xenon using caesium. It is however to be expected that in the future lasers with power levels of about 100 watts at the caesium wavelength will be developed. Probably caesium will then be preferentially used for the polarisation of inert gases.

The state of the art is that a gas mixture at a pressure typically of 7 to 10 bars is slowly passed through a cylindrical glass cell. The gas mixture consists 98 percent of $^4$Helium, one percent nitrogen and one percent of xenon. The typical flow rates for the gas mixture are a few cc per second.

The gas mixture first flows through a vessel (hereinafter termed "feed vessel") which contains ca. one gram of rubidium. The feed vessel with the rubidium present in it, together with the glass cell connected to it, is heated to ca. 100 to 150 degrees centigrade. By the provision of these temperatures, the rubidium is vaporised. The concentration of the vaporised rubidium atoms in the gas phase is determined by the temperature in the feed vessel. The gas flow transports the vaporised rubidium atoms from the feed vessel into the cylindrical sample cell. A powerful, circularly polarised laser (100 watts power in continuous operation) irradiates the sample cell, which is generally a glass cell, axially and optically pumps the rubidium atoms into a highly polarised state.

Here, the wavelength of the laser must be matched to the optical absorption line of the rubidium atoms (D1 line) In other words: in order optimally to transfer the polarisation of light to an alkali metal atom, the frequency of the light must coincide with the resonance frequency of the optical transition. The sample cell is located in a static magnetic field $B_0$ of a few tens of Gauss, which is created by coils, in particular a so-called Helmholtz coil pair. The direction of the magnetic field runs parallel to the cylinder axis of the sample cell, i.e. parallel to the direction of the laser beam. The magnetic field serves to control the polarised atoms.

The rubidium atoms optically highly polarised by the light of the laser collide in the glass cell inter alia with the xenon atoms and give up their high polarisation to the xenon atoms. At the exit of the sample cell, the rubidium is deposited on the wall, owing to its high melting point compared to the melting points of the other gases. The polarised xenon or the gas mixture is passed on from the sample cell into a freezing trap. This consists of a glass flask, the end of which is immersed in liquid nitrogen. The glass flask is moreover located in a magnetic field with a strength of 1000 to 2000 Gauss. The highly polarised xenon gas is deposited as ice on the inner glass wall of the freezing trap. At the outlet of the freezing trap, the remaining gas (helium and nitrogen) is passed through a needle valve and finally released.

The flow rate in the whole apparatus can be controlled with the needle valve, and measured with a gauge. If the flow rate increases too much, no time remains for the transfer of the polarisation from the rubidium atoms to the xenon atoms. Hence no polarisation is achieved. If the flow rate is too low, then too much time elapses before the desired amount of highly polarised xenon has been frozen. Thus the polarisation of the xenon atoms again declines through relaxation. The relaxation of the xenon atoms is greatly retarded by the freezing and by the strong magnetic field, to which the freezing trap is exposed. Hence it is necessary to freeze the inert gas as quickly and with as little loss as possible after the polarisation. The relaxation admittedly cannot be avoided by the freezing. However, there still remain 1 to 2 hours before the polarisation has declined so much that a subsequent use of the initially highly polarised gas is no longer possible.

A polariser of the aforesaid type always has joints. Joints are places at which at least two pipes through which the polarised gas is passed are joined together. The pipes as a rule consist of glass. The joint is created by a connecting element, such as e.g. flanges.

The light of the laser, which creates the polarisation, is absorbed in the sample cell. The intensity of the light and hence the polarisation of the alkali metal atoms in the sample cell decreases correspondingly. For technical reasons, the cross-section of the sample cell is not in general uniformly illuminated by the light of the laser. Consequently, the alkali metal atoms are not uniformly polarised. Interactions with the walls of the sample cell likewise alter the polarisation of the alkali metal atoms along the cross-section of the sample cell. Consequently, the polarisation of the alkali metal atoms in the sample cells varies depending on location.

For the control and analysis of the polarisation of inert gases, it is necessary to measure this as a function of the location in the sample cell. From the paper S. Appelt et al., Phys. Rev. A 58, 1412 (1998) and from A. Ben-Amar Baranga et al., Phys. Rev. A 58, 2282 (1998), measurement of the absolute polarisation of the alkali metal atoms as a function of location as follows is known.

RF coils are mounted on both sides of the sample cell. By means of these coils, an oscillating magnetic field is created in the sample cell. The oscillating magnetic field created by the RF coils is overlaid by the static magnetic field $B_0$ created by the Helmholtz coils. The magnetic field lines of the static magnetic field run parallel to the longitudinal axis of the cylindrical sample cell. The magnetic field lines of the oscillating magnetic field of frequency; $\omega_{RF}$ run perpendicular to this. The interaction of the two magnetic fields in the sample cell has the result that a precessing cone of the electron spin polarisation of the alkali metal atoms arises when the frequency of the RF magnetic field coincides with the Larmor frequency of the total spin of the rubidium atom.

The magnetic field $B_0$ is continuously varied, so that the cone arises on attainment of the Larmor frequency, and disappears again when the Larmor frequency is left. Alternatively, the frequency of the RF magnetic field could be correspondingly scanned at constant $B_0$ field.

For the detection of the cone, a titanium-sapphire laser, which creates circularly polarised light, irradiates the sample cell perpendicularly to the longitudinal axis. This light interacts with the transverse component of the cone. The light absorption is dependent on the presence of the cone. A photodetector is mounted on the opposite side of the sample cell in such a way that it measures the light of the laser. The photodetector "sees" the rotating transverse component of the cone as a modulation signal with the frequency $\omega$RF The signal of the photodetector is demodulated, so that the signal is then described by a resonance curve. With a low field $B_0$, the resonance curve shows only one resonance frequency in the form of one peak. For large magnetic fields $B_0$, that is magnetic fields typically of 30 Gauss and over, a large number of resonance frequencies can be measured. From this signal, the absolute polarisation of the alkali metal atoms is determined.

In order to be able to measure the absolute polarisation of the alkali metal atoms along the cross-section of the sample cell perpendicular to the magnetic field lines of the $B_0$ field (in the x-direction), a gradient coil is also provided, with which a gradient in the $B_0$ field is created in the sample cell. By this means, location information is encoded: the polarisation can then be determined as a function of the x-direction of the sample cell.

The device has the disadvantage that the polarisation can only be measured as a function of location along the x-direction. Also disadvantageous is the fact that a very expensive titanium-sapphire laser must be used. The use of an inexpensive laser diode was hitherto found to be impossible.

An object of the invention is the creation of an improved measurement device of the type mentioned at the outset for measurement of the absolute polarisation of alkali metal atoms in the sample cell.

SUMMARY OF THE INVENTION

The invention has particular application in a polarizer for inert gas wherein alkali metal atoms transfer polarization to the inert gas and polarization of the alkali metal atoms is laser detected. The disclosed apparatus and methods of operation provide improved polarization measurements.

The device includes a sample cell and also in one form of the invention means of polarizing alkali metal atoms in the sample cell. By means of Helmholtz coils (coil pair), the $B_0$ magnetic field, whose magnetic field lines run along a direction which is referred to hereinafter as the z-direction, is created in the sample cell. RF-coils are provided, which create an oscillating magnetic field perpendicular to the z-direction. This direction is referred to hereinafter as the x-direction. The circularly polarized light of a laser, hereinafter also referred to as the detection laser, shines through the sample cell in the x-direction. By means of a sensor —in particular a photodetector—the intensity of the light after passing through the sample cell is measured, the measured signal is fed into an electronic processor and thus the polarization of the alkali metal atoms in the sample cell is determined.

In one embodiment of the invention, a laser can irradiate the sample cell in the z-direction. It,the light of the laser is previously circularly polarised with a λ/4 plate, then the alkali metal atoms in the sample cell are polarised.

Means for controlling the temperature of the detection laser are provided. In particular, the means include a temperature sensor, with which the temperature of the detection laser is measured. Further, the means include a heating/cooling device, with which the detection laser can be heated or cooled as required. The heating/cooling device is controlled by a control device depending on the measured temperature of the detection laser. By the aforesaid means, the temperature of the laser is kept constant.

It has been found that the maintenance of a constant temperature results in improved measurement results. Further, a sufficiently constant temperature is a prerequisite in order to be able to use an inexpensive semiconductor diode as detection laser instead of a titanium-sapphire laser. In particular, improved measurement results are obtained with the use of the semiconductor diode.

In one form of the invention, the means for the maintenance of a constant temperature are so designed that the temperature fluctuations are not more than one thousandth of a degree centigrade per hour.

In order to keep temperature fluctuations at the laser as small as possible, in a further form of the invention the laser is embedded in a heat-conducting metal, in particular in copper. The heat capacity of the metal is then very much greater than the heat capacity of the laser. Temperature fluctuations of the laser are cushioned by the metal. In this way, it is possible to maintain the desired high constancy of temperature. It has been found that the temperature constancy is an essential measure for achieving good measurement results. In particular, the volume of the metal should be several times greater than the volume of the laser.

In a further form of the invention, a Peltier element is used to heat or cool the laser as required. In order to function perfectly, the Peltier element is then in particular in contact with a heat sink. The heat sink generally has so-called cooling fins, which ensure a large surface area and hence rapid removal of heat.

In a further form of the invention, an electronic system is provided, which keeps the current with which laser provided for the detection of the alkali metal polarlsation is operated constant. This supply current for the laser should in particular fluctuate by less than 10 ppm. A suitable electronic system, which fulfils the requirements, is described in the paper "Rev. Sci. Instrum. 61 (8), August 1990". Through this further form of the invention, the measurement result is further improved.

In a further form of the invention, a semiconductor diode, in particular a "mono mode laser diode" is used as the laser for the detection of the polarisation of the alkali metal atoms as a function of location. Such a laser is considerably cheaper than the titanium-sapphire laser used in the state of the art. The price difference amounts at present to a factor of ca. 100 to 1000. Further, it has been found that with the laser which consists of a semiconductor diode better results compared to a titanium-sapphire laser are obtained, when the temperature and the supply current are stabilised in the aforesaid manner. The amplitude noise of the laser consisting of the semiconductor diode is then very much less than the amplitude noise of a dye- or a titanium-sapphire laser. The frequency noise of the laser consisting of the semiconductor diode is similar to the frequency noise of a non-stabilised titanium-sapphire laser, if the aforesaid measures for the stabilisation of the temperature and the supply current are taken. Because of the improved amplitude noise, better measurement results compared to the state of the art are obtained. A semiconductor diode is small and light compared to a titanium-sapphire laser. Even with the use of a metal block which has a much greater heat capacity than the diode, the assembly is small and light compared to a titanium-sapphire laser. The assembly according to the invention with the semiconductor diode is thus especially mobile, which is of especial advantage in a particular application mentioned below.

In a further form of the invention, the semiconductor diode is a single (mono) mode laser diode with a power of for example ca. 20 milliwatts. By this choice, the frequency stability is advantageously ensured. The wavelength at which the semiconductor diode emits light is in particular about 795 nanometres.

In a further form of the invention, the semiconductor diode together with the detector lying opposite is mounted onto a carriage displaceable in the z-direction. By displacement of the carriage relative to the sample cell, the polarisation of the alkali metal atoms in the sample cell is in addition measured in the z-direction. A two-dimensional picture of the absolute polarisation of the alkali metal atoms is thus obtained.

The carriage can be a plate rolling on rails, on which are mounted the semiconductor diode together with the detector or sensor lying opposite and the further optical elements, when necessary, such as lenses, mirrors, and linear or circular polarisers. Further, in particular, the gradient coil is mounted on such a carriage. This enables rapid and uncomplicated measurement of two-dimensional pictures of the rubidium polarisation.

The measurement results enable optimal adjustment and control of the polarisation device, in order to polarise inert gases as efficiently as possible.

In a further advantageous form of the invention, the device has gradient coils which extend over a considerably greater volume (for example over twice as great a volume) than the volume of the sample cell. By this means, it is possible to provide an almost linear gradient ($dB_0/dx=$ constant) of the $B_0$ magnetic field. Then not only can the measurement signal be evaluated in a particularly simple manner, but in addition it is also ensured that unambiguous assignment of polarisation to a location x is possible.

DESCRIPTION OF PREFERRED EMBODIMENTS

Below, the invention is explained in more detail on the basis of FIGS. 1 and 2.

FIG. 1 shows a part of the design of a polariser for inert gases with the measurement device according to the invention. A gas mixture of the type mentioned at the outset is passed through a sample cell 1 in the z-direction, that is in the longitudinal direction of the sample cell. The sample cell is irradiated in the longitudinal direction by a laser 2. This laser 2 has a power of ca. 100 watts. It emits circularly polarised light with a wavelength of 795 nanometres. By means of this laser 2, the alkali metal atoms in the gas mixture are polarised.

Looking in the z-direction, one of the coil bobbins of the Helmholtz coils in situated in front of and one behind the sample cell. By means of the Helmholtz coils, a static $B_0$ field, whose magnetic field lines run in the z-direction, is provided in the sample cell. One RF coil 4 is located directly next to each side of the sample cell 1. By means of the two RF coils 4, an oscillating magnetic field, whose magnetic field lines run perpendicular to the z-direction, is created in the sample cell. This direction is referred to as the x-direction. At a distance from the sample cell, gradient coils 5 are provided, with which a magnetic field, which varies linearly in the x-direction, is provided parallel to the $B_0$ field in the sample cell. The space spanned by the gradient coils is at least twice as great as the volume of the sample cell 1. By means of a laser diode with a power of ca. 20 milliwatts and a wavelength of 795 nanometres, linearly polarised light is created. The light from the laser diode 6 falls onto a mirror 7, which deflects the light so that this passes through the sample cell 1 in the x-direction. Between the mirror 7 and the sample cell 1, a λ/4 plate is inserted in the light beam of the laser 2. The light of the laser is circularly polarised by this. After passing through the sample cell, the light of the laser is focused and passed on to a photodiode 9.

A HF amplifier 11 is connected after a synthesiser 10. The signal of the synthesiser 10 thus amplified is transferred to the RF coils 4 (RF: radio frequency). The frequency of the radio frequency irradiation is typically about 25 MHz and the sine wave power is 8 watts. At the same time, the synthesiser 10 supplies a reference signal to a lock-in amplifier 12. The electrical signal deriving from the photodiode 9 is also passed on to the lock-in amplifier 12. This has the effect that the noise is filtered out. The signal is passed on to an oscilloscope 13. The oscilloscope 13 serves for the display of the result, from which the spatial distribution of the alkali metal polarisation in the sample cell-is determined.

A synthesiser 14 supplies a sawtooth voltage. The sawtooth voltage controls a constant-current source 15. This supplies a current to the Helmholtz coils (Helmholtz coil pair) 3, so that the magnetic $B_0$ field of ca. 50 Gauss is created, which varies with time in the sample cell by ca. ±25 Gauss in a sawtooth pattern.

By means of a constant current source 16, the gradient coils 5 are supplied with a constant current.

The operation of the device so far described by way of example leads to the determination of a polarisation P as a function of x, described by a function P=P(x).

The laser diode 6, the photodiode 9 next to the lens 8, the lambda/4 plate 28 and the mirror 7 are located on an aluminium plate 17, which can be displaced in the z-direction relative to the sample cell 1 (carriage). If the aluminium plate 17 is displaced in the z-direction, then the polarisation in the sample cell is additionally determined as a function of the location z. Thus overall the polarisation P=P(x, z) can be determined.

The aforesaid assembly is essentially mounted on a baseplate 18. The sample cell 1 is located in a container 19, which serves for heat insulation.

Figure 2:
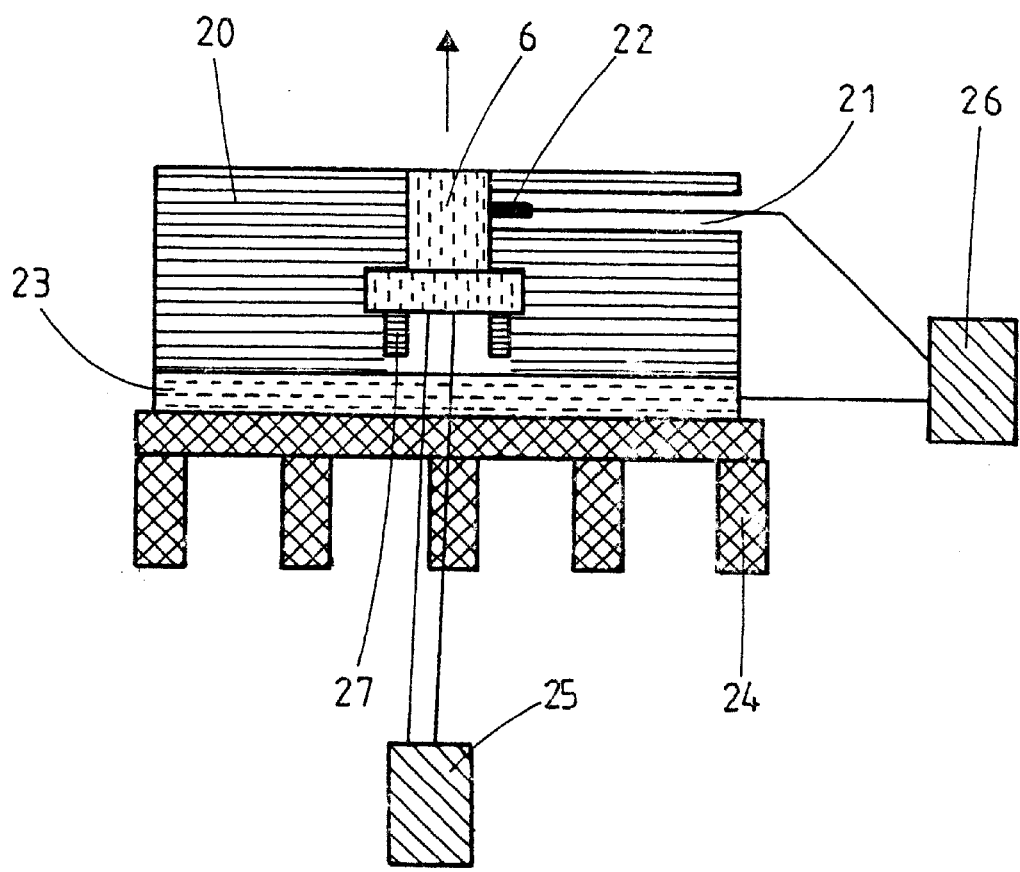

FIG. 2 illustrates in section the design of the laser diode 6 from FIG. 1. The actual laser diode 6 is embedded in a block 20 consisting of copper. A brass ring 27 with external thread is screwed into the block 20 so that the detection laser 6 fits closely to the block 20 and thus good heat transfer is ensured. The copper block 20 occupies a volume which is very much greater than the volume of the laser diode 6. A drill-hole 21, which extends to the laser diode 6, is provided in the block 20. A very small thermoelement (thermistor) is glued to the point of a guide rod. The thermoelement together with the guide rod is pushed into the drill-hole 21. In this way, the temperature specifically of the laser diode is measured instantaneously. A Peltier element is mounted on the underside of the block consisting of copper 20. The Peltier element 23 is in turn joined to a heat sink 24. The heat sink is characterised in particular by cooling fins, so that the heat sink 24 has a very large area.

Depending on the temperature measured by the thermoelement 22, the Peltier element 23 is supplied with current in such a way that the temperature of the laser diode 6 is kept constant. The fluctuations in the temperature should not exceed one thousandth of a degree centigrade per hour.

The laser diode 6 is supplied with power via a commercially available current smoother 25, which supplies a current of 100 mA ±1 μA/hr. As a temperature regulator 26, that known from the paper "Rev. Sci. Instrum. 61 (8), Aug. 1990" is used.

What we claim is:

1. A device for the determination of the absolute polarization of alkali metal atoms, said device including a sample cell for uptake of alkali metal, a coil pair for creation of a $B_0$ magnetic field in the sample cell, coils which create an oscillating magnetic field perpendicular to the magnetic field lines of the $B_0$ magnetic field, a semiconductor diode laser for detecting the polarization of the alkali metal atoms, said laser being arranged to pass light through the sample cell perpendicular to the magnetic field lines of the $B_0$ magnetic field, a sensor for measuring the intensity of the light after passage through the sample cell and providing a signal corresponding with the measured intensity, an electronic processor for evaluating the signal measured by the sensor and thereby determining the absolute polarization of alkali metal atoms in the sample cell, a carriage displaceable parallel to the magnetic field lines of the $B_0$ field having said laser and sensor mounted on said carriage, and means for controlling the temperature of the laser, the means including an electronic system providing a constant current for operating the laser, a temperature sensor for measuring the temperature of the laser, a heating/cooling device for heating or cooling the laser, and a control device for controlling the heating cooling device depending on the measured temperature of the laser to maintain the laser temperature so that laser temperature fluctuations do not exceed one thousandth of a degree centigrade per hour.

2. The device of claim 1, wherein said sample cell has a volume and further including gradient coils which enclose a volume that is at least twice as great as the volume of the sample cell, the gradient coils creating a substantially linear gradient in the $B_0$ magnetic field in the samples cell.

3. The device of claim 2, wherein the laser is embedded in a heat conducting metal and said heating/cooling device includes a Peltier element mounted to said heat conducting metal adjacent to a heat sink.

4. The device of claim 3, wherein the heat conducting metal is copper.

5. The device of claim 1, wherein the laser is embedded in a heat conducting metal having a volume that exceeds the volume of the embedded laser at least by a factor of 1.

6. The device of claim 5, wherein the volume of the heat conducting metal exceeds the volume of the embedded laser by a factor of 3.

7. The device of claim 1, wherein said heating/cooling device comprises a Peltier element adjacent to a heat sink.

8. The device of claim 7, wherein said Peltier element is mounted to said heat conducting metal and adjacent to said heat sink.

9. The device of claim 7, wherein said sample cell has a volume and further including gradient coils which enclose a volume that is at least twice as great as the volume of the sample cell, the gradient coils creating a substantially linear gradient in the $B_0$ magnetic field in the samples cell.

10. The device of claim 9, further including a thermally insulating housing in which the laser is located.

11. The device of claim 1, wherein said semiconductor diode laser is a mono mode laser diode with a power of about 20 milliwatts and a wavelength of about 795 nanometres.

12. The device of claim 1, further including at least one of a lense, mirror and circular polarizer and wherein the at least one lense, mirror and circular polarizer is also mounted in said carriage.

13. The device of claim 1, wherein the sample cell is a component of a polarizer for an inert gases.

14. A method for determining the absolute polarization of alkali metal atoms in a sample cell for uptake of alkali metal, the cell having a longitudinal direction along which said alkali metal atoms move, comprising the steps of creating a $B_0$ magnetic field in the sample cell having magnetic field lines aligned with the longitudinal axis of the sample cell, creating an oscillating magnetic field perpendicular to the magnetic field lines of the $B_0$ magnetic field, passing a semiconductor diode laser light through the sample cell perpendicular to the magnetic field lines of the $B_0$ magnetic field to detect polarization of alkali metal atoms, measuring the intensity of the light after passage through the sample cell with a sensor that provides a signal corresponding with the measured intensity, evaluating the signal measured by the sensor with an electronic processor and thereby determining the absolute polarization of alkali metal atoms in the sample cell, controlling the temperature of the laser by measuring the temperature of the laser, heating or cooling the laser in accordance with the measured temperature of the laser, controlling the heating or cooling depending on the measured temperature of the laser to maintain the laser temperature substantially constant so that laser temperature fluctuations do not exceed one thousandth of a degree centigrade per hour, and moving said laser and said sensor parallel to the magnetic field lines of the $B_0$ field to determine polarization in said sample cell as a function of locations along directions both parallel and perpendicular to the sample cell.

15. A method for determining the absolute polarization of alkali metal atoms in a sample cell for uptake of alkali metal, the cell having a longitudinal direction along which said alkali metal atoms move, comprising the steps of creating a $B_0$ magnetic field in the sample cell having magnetic field lines aligned with the longitudinal axis of the sample cell, creating an oscillating magnetic field perpendicular to the magnetic field lines of the $B_0$ magnetic field, passing a semiconductor diode laser light through the sample cell perpendicular to the magnetic field lines of the $B_0$ magnetic field to detect polarization of alkali metal atoms, measuring the intensity of the light after passage through the sample cell with a sensor that provides a signal corresponding with the measured intensity, evaluating the signal measured by the sensor with an electronic processor and thereby determining the absolute polarization of alkali metal atoms in the sample cell, controlling a supply current operating the laser so that current fluctuates less than 10 ppm, and moving said laser and said sensor parallel to the magnetic field lines of the $B_0$ field to determine polarization in said sample cell as a function of locations along directions both parallel and perpendicular to the sample cell.

16. The method of claim 15, further including the steps of controlling the temperature of the laser by measuring the temperature of the laser, heating or cooling the laser in accordance with the measured temperature of the laser, and controlling the heating or cooling depending on the measured temperature of the laser to maintain the laser temperature substantially constant so that laser temperature fluctuations do not exceed one thousandth of a degree centigrade per hour.

\* \* \* \* \*

UNITED STATES PATENT AND TRADEMARK OFFICE
CERTIFICATE OF CORRECTION

PATENT NO. : 6,589,793 B1  Page 1 of 1
DATED : July 8, 2003
INVENTOR(S) : Stephan Appelt et al.

It is certified that error appears in the above-identified patent and that said Letters Patent is hereby corrected as shown below:

<u>Title page,</u>
Item [75], Inventor, "Nadim Jone Shah" should be -- Nadim Joni Shah --.
Item [30], Foreign Application Priority Data, "June 18, 1919" should be -- June 18, 1999 --.

<u>Column 8,</u>
Line 59, delete "nonometres" and insert -- nanometers --.

Signed and Sealed this

Ninth Day of December, 2003

JAMES E. ROGAN
*Director of the United States Patent and Trademark Office*